United States Patent
Inokuchi et al.

(10) Patent No.: US 8,703,163 B2
(45) Date of Patent: Apr. 22, 2014

(54) WATER-REPELLENT FINE PARTICLES AND MAKING METHOD

(71) Applicant: Shin-Etsu Chemical Co., Ltd., Tokyo (JP)

(72) Inventors: Yoshinori Inokuchi, Annaka (JP); Ryuji Horiguchi, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/688,913

(22) Filed: Nov. 29, 2012

(65) Prior Publication Data

US 2013/0090448 A1   Apr. 11, 2013

Related U.S. Application Data

(62) Division of application No. 12/700,346, filed on Feb. 4, 2010, now abandoned.

(30) Foreign Application Priority Data

Feb. 6, 2009   (JP) ................. 2009-025529

(51) Int. Cl.
*A61K 8/02*   (2006.01)
*C08G 77/12*   (2006.01)

(52) U.S. Cl.
USPC .......................................... 424/401; 528/31

(58) Field of Classification Search
USPC .......................................... 424/401; 528/31
See application file for complete search history.

(56) References Cited

U.S. PATENT DOCUMENTS

| 5,538,793 | A  | 7/1996  | Inokuchi et al. |
| 7,344,783 | B2 | 3/2008  | Shea |
| 8,133,586 | B2 | 3/2012  | Inokuchi et al. |
| 8,293,366 | B2 | 10/2012 | Inokuchi et al. |
| 2010/0203118 | A1 | 8/2010 | Tanaka et al. |

FOREIGN PATENT DOCUMENTS

| EP | 0 661 334 A1 | 7/1995 |
| EP | 2 182 022 A1 | 5/2010 |
| EP | 2 182 023 A1 | 5/2010 |
| JP | 7-196815 A   | 8/1995 |
| JP | 2007-126609 A | 5/2007 |

OTHER PUBLICATIONS

Arkles, Barry. "Hydrophobicity, Hydrophilicity and Silanes . . . " Paint and Coatings Industry Magazine, Oct. 1, 2006.
European Search Report dated Jun. 30, 2010, issued in connection with European Patent Application No. 10250208.5.
Japanese Office Action for Application No. 2009-025529 dated Apr. 27, 2011.

*Primary Examiner* — Aradhana Sasan
(74) *Attorney, Agent, or Firm* — Birch, Stewart, Kolasch & Birch, LLP

(57) ABSTRACT

Silicone elastomer spherical particles having a volume mean particle size of 0.1-100 μm are coated with a polyorganosilsesquioxane and washed with alcohol or a mixture of alcohol and water. The coated fine particles are water repellent so that they are non-dispersible in water and float on water.

21 Claims, No Drawings

WATER-REPELLENT FINE PARTICLES AND MAKING METHOD

CROSS-REFERENCE TO RELATED APPLICATION

This application is a Divisional of co-pending application Ser. No. 12/700,346, filed on Feb. 4, 2010. Priority is also claimed to Japanese Application No. 2009-025529, filed on Feb. 6, 2009. The entire contents of each of these applications is hereby incorporated by reference.

TECHNICAL FIELD

This invention relates to water repellent fine particles in the form of silicone elastomer spherical fine particles coated with polyorganosilsesquioxane and a method for preparing the same.

BACKGROUND ART

From the past, silicone particles are used in cosmetics for the purpose of imparting extensibility and pleasant feels on use like smoothness and silkiness. In particular, fine particles comprising silicone elastomer spherical fine particles coated with polyorganosilsesquioxane as disclosed in JP-A H07-196815 are used in many cosmetics because of a soft feel, anti-agglomerative and dispersive properties.

Solid powder cosmetics suffer from a makeup smearing phenomenon that the cosmetic film on the skin changes color or loses evenness when wetted with water or perspiration. Water repellent powder is generally used in order to prevent the makeup smearing phenomenon. However, the fine particles comprising silicone elastomer spherical fine particles coated with polyorganosilsesquioxane are less water repellent because surfactant is carried over from the manufacturing process.

CITATION LIST

Patent Document 1: JP-A H07-196815

SUMMARY OF INVENTION

An object of the invention is to provide water-repellent fine particles in the form of silicone elastomer spherical fine particles coated with polyorganosilsesquioxane and a method for preparing the same.

In one aspect, the invention provides water repellent fine particles comprising 100 parts by weight of silicone elastomer spherical particles having a volume mean particle size of 0.1 to 100 μm, which are coated with 0.5 to 25 parts by weight of a polyorganosilsesquioxane, the fine particles being non-dispersible in water and floatable on water.

In a preferred embodiment, trimethylsilyl groups are pendant to the surface of the polyorganosilsesquioxane coating. In a preferred embodiment, hydrolytic condensation reaction between a tetraalkoxysilane and at least one silylating agent selected from trimethylalkoxysilane, trimethylsilanol and hexamethyldisilazane has been carried out on the surface of the polyorganosilsesquioxane coating.

In another aspect, the invention provides a method for preparing water repellent fine particles comprising the steps of providing a dispersion of silicone elastomer spherical particles having a volume mean particle size of 0.1 to 100 μm in water using a surfactant; adding an organotrialkoxysilane to the water dispersion and effecting hydrolytic condensation reaction thereof in the dispersion in the presence of an alkaline substance for coating the silicone elastomer particles with polyorganosilsesquioxane; and washing the coated particles with alcohol or a mixture of alcohol and water to remove the surfactant.

The method may further comprise, after the step of effecting hydrolytic condensation reaction of organotrialkoxysilane, the step of adding a tetraalkoxysilane and at least one silylating agent selected from trimethylalkoxysilane, trimethylsilanol and hexamethyldisilazane to the dispersion and effecting hydrolytic condensation reaction thereof in the dispersion.

ADVANTAGEOUS EFFECTS OF INVENTION

Silicone elastomer spherical fine particles are coated with a polyorganosilsesquioxane to form coated fine particles which are highly water repellent.

DESCRIPTION OF EMBODIMENTS

Water-repellent fine particles are obtained by coating silicone elastomer spherical fine particles with a polyorganosilsesquioxane. The silicone elastomer spherical particles should have a volume mean particle size of 0.1 to 100 μm. Particles with a size of less than 0.1 μm fail to produce a silky feel or smoothness whereas particles with a size of more than 100 μm adversely affect a silky feel or smoothness and rather produce a gritty feel. The preferred particle size is in a range of 1 to 40 μm. It is noted that the volume mean particle size is measured by the electric resistance method.

The silicone elastomer is a cured form of silicone compound comprising linear organosiloxane blocks of the formula: $—(R^1_2SiO_{2/2})_n—$, having rubber elasticity and tack-free. In the formula, $R^1$ is a substituted or unsubstituted, monovalent hydrocarbon group of 1 to 30 carbon atoms, and n is a positive number of 5 to 5,000. Suitable groups of $R^1$ include alkyl groups such as methyl, ethyl, propyl, butyl, pentyl, hexyl, heptyl, octyl, decyl, undecyl, dodecyl, tetradecyl, pentadecyl, hexadecyl, heptadecyl, octadecyl, nonadecyl, eicosyl, heneicosyl, docosyl, tricosyl, tetracosyl, and triacontyl; aryl groups such as phenyl, tolyl and naphthyl; aralkyl groups such as benzyl and phenethyl; alkenyl groups such as vinyl and allyl; cycloalkyl groups such as cyclopentyl, cyclohexyl and cycloheptyl; and substituted forms of the foregoing hydrocarbon groups in which some or all of hydrogen atoms attached to carbon atoms are substituted by atoms such as halogen atoms (e.g., fluorine, chlorine, bromine and iodine) and/or substituent groups such as acryloyloxy, methacryloyloxy, epoxy, glycidoxy and carboxyl.

The silicone elastomer preferably has a rubber hardness of 5 to 90 as measured by type A Durometer according to JIS K-6253. A hardness of less than 5 may lead to strong agglomeration and a lack of fluidity, dispersion, silky feel and smoothness whereas a hardness of more than 90 may lead to a lack of soft feel. The preferred rubber hardness is in a range of 10 to 80.

The silicone elastomer is obtainable from a curable liquid silicone. Cure reaction may be, for example, condensation reaction between methoxysilyl ($≡SiOCH_3$) and hydroxysilyl ($≡SiOH$), radical reaction between mercaptopropylsilyl ($≡Si—C_3H_6SH$) and vinylsilyl ($≡SiCH=CH_2$), or addition reaction between vinylsilyl ($≡SiCH=CH_2$) and hydrosilyl ($≡SiH$), with the addition reaction being preferred for reactivity.

When silicone elastomers are formed by addition reaction curing, a liquid silicone composition is prepared by combining an organopolysiloxane of the average formula: $R^2{}_aR^3{}_bSiO_{(4-a-b)/2}$ containing at least two monovalent olefinic unsaturated groups in the molecule with an organohydrogenpolysiloxane of the average formula: $R^4{}_cH_dSiO_{(4-c-d)/2}$ containing at least three silicon-bonded hydrogen atoms in the molecule or by combining an organopolysiloxane of the average formula: $R^2{}_aR^3{}_bSiO_{(4-a-b)/2}$ containing at least three monovalent olefinic unsaturated groups in the molecule with an organohydrogenpolysiloxane of the average formula: $R^4{}_cH_dSiO_{(4-c-d)/2}$ containing at least two silicon-bonded hydrogen atoms in the molecule. In either case, the organopolysiloxane and the organohydrogenpolysiloxane are blended in such amounts as to give 0.5 to 2 hydrosilyl groups per monovalent olefinic unsaturated group. The liquid silicone composition may undergo addition polymerization in the presence of a platinum catalyst.

In the above formulae, $R^2$ is a substituted or unsubstituted, monovalent hydrocarbon group of 1 to 30 carbon atoms, excluding aliphatic unsaturated group, and $R^3$ is a monovalent olefinic unsaturated group of 2 to 6 carbon atoms. The subscripts a and b are positive numbers in the range: $0<a<3$, $0<b\leq3$, and $0.1\leq a+b\leq3$, and preferably $0<a\leq2.295$, $0.005\leq b\leq2.3$, and $0.5\leq a+b\leq2.3$. $R^4$ is a substituted or unsubstituted, monovalent hydrocarbon group of 1 to 30 carbon atoms, excluding aliphatic unsaturated group. The subscripts c and d are positive numbers in the range: $0<c<3$, $0<d\leq3$, and $0.1\leq c+d\leq3$, and preferably $0<c\leq2.295$, $0.005\leq d\leq2.3$, and $0.5\leq c+d\leq2.3$.

Suitable groups of $R^2$ include alkyl groups such as methyl, ethyl, propyl, butyl, pentyl, hexyl, heptyl, octyl, decyl, undecyl, dodecyl, tetradecyl, pentadecyl, hexadecyl, heptadecyl, octadecyl, nonadecyl, eicosyl, heneicosyl, docosyl, tricosyl, tetracosyl, and triacontyl; aryl groups such as phenyl, tolyl and naphthyl; aralkyl groups such as benzyl and phenethyl; cycloalkyl groups such as cyclopentyl, cyclohexyl and cycloheptyl; and substituted forms of the foregoing hydrocarbon groups in which some or all of hydrogen atoms attached to carbon atoms are substituted by atoms such as halogen atoms (e.g., fluorine, chlorine, bromine and iodine) and/or substituent groups such as acryloyloxy, methacryloyloxy, epoxy, glycidoxy and carboxyl. It is preferred from the industrial aspect that methyl account for at least 50 mol % of entire $R^2$ groups.

Suitable groups of $R^3$ include vinyl, allyl, propenyl, butenyl, pentenyl and hexenyl, with vinyl being preferred from the industrial aspect.

Suitable groups of $R^4$ are as exemplified for $R^2$.

The organopolysiloxane containing olefinic unsaturated groups and the organohydrogenpolysiloxane preferably have a viscosity at 25° C. of up to 100,000 mm$^2$/s, and more preferably up to 10,000 mm$^2$/s. A viscosity in excess of 100,000 mm$^2$/s may make it difficult to form particles having a narrow particle size distribution by the method to be described later. Notably the viscosity is measured by a capillary viscometer. The organopolysiloxane containing olefinic unsaturated groups and the organohydrogenpolysiloxane may have linear, branched or cyclic structures, preferably linear structures.

As described above, an organopolysiloxane containing at least two monovalent olefinic unsaturated groups in the molecule must be combined with an organohydrogenpolysiloxane containing at least three silicon-bonded hydrogen atoms in the molecule. Alternatively, an organopolysiloxane containing at least three monovalent olefinic unsaturated groups in the molecule must be combined with an organohydrogenpolysiloxane containing at least two silicon-bonded hydrogen atoms in the molecule. These combinations are essential because reaction of olefinic unsaturated groups with hydrosilyl groups in respective molecules would otherwise fail to form a tack-free elastomer or cured product.

As described above, the organopolysiloxane having olefinic unsaturated groups and the organohydrogenpolysiloxane must be blended in such amounts as to give 0.5 to 2 silicon-bonded hydrogen atoms per olefinic unsaturated group. Blending ratios giving less than 0.5 or more than 2 silicon-bonded hydrogen atoms fail to form a tack-free elastomer or lead to a highly reactive elastomer. Blending ratios to give 0.7 to 1.5 silicon-bonded hydrogen atoms per olefinic unsaturated group are preferred.

The silicone elastomer spherical fine particles used herein may contain therein silicone fluid, organosilane, inorganic powder or organic powder.

Surface coating of particles with another material belongs to the composite particle technology and may be achieved by several methods. For example, cover particles may be attached to surfaces of core particles by dry mixing of core particles and cover particles. By further applying impact forces, compression forces, frictional forces or shear forces, the cover particles may be fixed to the core particles or consolidated as a cover film over the core particles. Since silicone elastomer particles are strongly agglomerative, it is difficult to thinly and uniformly attach cover particles to surfaces of silicone elastomer core particles by dry mixing. Additionally, since silicone elastomer particles are elastic, it is impossible to fix cover particles to silicone elastomer core particles by applying impact forces, compression forces, frictional forces or shear forces. Another method of preparing coated particles is by spray drying a dispersion of core particles and cover particles, but there are often produced agglomerated particles, or separate core particles and cover particles. Then fine particles comprising silicone elastomer spherical fine particles coated with polyorganosilsesquioxane according to the invention are produced by the method of JP-A H07-196815. Namely, silicone elastomer spherical fine particles are coated with polyorganosilsesquioxane by dispersing silicone elastomer spherical fine particles in water with the aid of a surfactant to form a water dispersion, and effecting hydrolytic condensation reaction of an organotrialkoxysilane in the water dispersion.

A water dispersion of silicone elastomer spherical fine particles may be prepared by any well-known methods. For example, when a silicone elastomer is formed by addition reaction curing, the desired dispersion may be prepared by adding a surfactant and water to a liquid silicone composition comprising the organopolysiloxane having olefinic unsaturated groups and the organohydrogenpolysiloxane, both described above, emulsifying the mixture, adding a platinum base catalyst to the resulting emulsion, and effecting addition polymerization.

The surfactant used herein is not particularly limited. Exemplary surfactants include nonionic surfactants such as polyoxyethylene alkyl ethers, polyoxyethylene polyoxypropylene alkyl ethers, polyoxyethylene alkyl phenyl ethers, polyethylene glycol fatty acid esters, sorbitan fatty acid esters, polyoxyethylene sorbitan fatty acid esters, polyoxyethylene sorbitol fatty acid esters, glycerol fatty acid esters, polyoxyethylene glycerol fatty acid esters, polyglycerol fatty acid esters, propylene glycol fatty acid esters, polyoxyethylene castor oil, polyoxyethylene hardened castor oil, polyoxyethylene hardened castor oil fatty acid esters, polyoxyethylene alkyl amines, polyoxyethylene fatty acid amides, polyoxyethylene-modified organopolysiloxane, polyoxyethylene/polyoxypropylene-modified organopolysiloxane;

anionic surfactants such as alkyl sulfates, polyoxyethylene alkyl ether sulfates, polyoxyethylene alkyl phenyl ether sulfates, N-acyltaurine acid salts, alkylbenzenesulfonates, polyoxyethylene alkyl phenyl ether sulfonates, α-olefinsulfonates, alkylnaphthalenesulfonic acid, alkyl diphenyl ether disulfonates, dialkyl sulfosuccinates, monoalkylsulfosuccinates, polyoxyethylene alkyl ether sulfosuccinates, fatty acid salts, polyoxyethylene alkyl ether acetates, N-acylamic acid salts, alkenylsuccinates, alkyl phosphates, polyoxyethylene alkyl ether phosphates, polystyrene sulfonates, naphthalene sulfonic acid-formalin condensates, aromatic sulfonic acid-formalin condensates, carboxylic acid polymers, and styrene-oxyalkylene-acid anhydride copolymers;

cationic surfactants such as alkyltrimethylammonium salts, dialkyldimethylammonium salts, polyoxyethylene alkyldimethylammonium salts, dipolyoxyethylene alkylmethylammonium salts, tripolyoxyethylene alkylammonium salts, alkylbenzyldimethylammonium salts, alkylpyridinium salts, monoalkylamine salts, monoalkylamideamine salts, and cationized cellulose; and ampholytic surfactants such as alkyldimethylamine oxides, alkyldimethylcarboxybetaines, alkylamidopropyldimethylcarboxybetaines, alkylhydroxysulfobetaines, and alkylcarboxymethylhydroxyethylimidazolinium betaines.

These surfactants may be used alone or in admixture of two or more although anionic surfactants should not be combined with cationic surfactants. The surfactant is preferably used in an amount of 0.01 to 20 parts by weight, more preferably 0.05 to 5 parts by weight per 100 parts by weight of the liquid silicone composition. Less than 0.01 pbw of the surfactant may fail to form fine particles whereas more than 20 pbw of the surfactant may interfere with the subsequent step of coating particles with polyorganosilsesquioxane resin.

Emulsification and dispersion may be performed using ordinary emulsifying and dispersing machines. Useful are high-speed centrifugal agitators such as Homo Disper®, high-speed shear agitators such as homo mixers, high-pressure injection emulsifier/dispersers such as homogenizers, colloid mills, and ultrasonic emulsifiers.

If the platinum base catalyst is less dispersible in water, a solution of the platinum base catalyst in a surfactant may be added to the emulsion. During the addition polymerization, the reaction temperature may be room temperature, but the emulsion may be heated below 100° C. if the reaction does not run to completion at room temperature.

In the fine particles resulting from coating of silicone elastomer spherical fine particles with polyorganosilsesquioxane according to the invention, there must be present 0.5 to 25 parts by weight of polyorganosilsesquioxane per 100 parts by weight of silicone elastomer spherical particles. On this basis, less than 0.5 pbw of polyorganosilsesquioxane leads to coated particles which tend to agglomerate and lack fluidity, dispersion, silky feel and smoothness whereas more than 25 pbw of polyorganosilsesquioxane leads to a lack of soft feel. The preferred range is 1 to 15 pbw.

The polyorganosilsesquioxane is a resinous solid product in which units: $R^5SiO_{3/2}$ are crosslinked in a three-dimensional network. Herein $R^5$ is substituted or unsubstituted, monovalent hydrocarbon group of 1 to 20 carbon atoms. Suitable groups of $R^5$ include alkyl groups such as methyl, ethyl, propyl, butyl, pentyl, hexyl, heptyl, octyl, decyl, undecyl, dodecyl, tetradecyl, pentadecyl, hexadecyl, heptadecyl, octadecyl, nonadecyl, and eicosyl; alkenyl groups such as vinyl and allyl; aryl groups such as phenyl, tolyl and naphthyl; aralkyl groups such as benzyl and phenethyl; cycloalkyl groups such as cyclopentyl, cyclohexyl and cycloheptyl; and substituted forms of the foregoing hydrocarbon groups in which some or all of hydrogen atoms attached to carbon atoms are substituted by atoms such as halogen atoms (e.g., fluorine, chlorine, bromine and iodine) and/or substituent groups such as amino, acryloyloxy, methacryloyloxy, epoxy, glycidoxy, mercapto and carboxyl. Preferably, methyl accounts for at least 50 mol %, more preferably at least 70 mol % of entire $R^5$ groups, for the purpose of coating silicone particles with the polyorganosilsesquioxane by the method described below. In addition to units: $R^5SiO_{3/2}$, the polyorganosilsesquioxane may further comprise units: $R^5_2SiO_{2/2}$ for the purposes of improving a soft feel or the like as long as the advantages of anti-agglomeration and dispersibility are not compromised.

According to the invention, silicone elastomer spherical fine particles are coated with polyorganosilsesquioxane by effecting hydrolytic condensation reaction of an organotrialkoxysilane in a water dispersion of silicone elastomer spherical fine particles which has been prepared using a surfactant. An alkaline substance is used as the catalyst for hydrolytic condensation reaction of organotrialkoxysilane. The alkaline substance is previously added to the water dispersion of silicone elastomer spherical fine particles in such amounts that the pH of the resulting dispersion is preferably in a range of 10.0 to 13.0, more preferably 10.5 to 12.5. If the pH of the water dispersion of silicone elastomer spherical fine particles is lower than 10.0, then effective hydrolytic condensation reaction of organotrialkoxysilane may not take place. If the pH of the dispersion is higher than 13.0, then coating of elastomer particles with polyorganosilsesquioxane may be interrupted.

The alkaline substance is not particularly limited. Useful examples include alkali metal hydroxides such as potassium hydroxide, sodium hydroxide and lithium hydroxide; alkaline earth metal hydroxides such as calcium hydroxide and barium hydroxide; alkali metal carbonates such as potassium carbonate and sodium carbonate; and amines such as ammonia, tetraammonium oxide, monomethylamine, monoethylamine, monopropylamine, monobutylamine, monopentamine, dimethylamine, diethylamine, trimethylamine, triethanolamine, and ethylenediamine. The alkaline substance may be added in the form of an alkaline aqueous solution. Inter alia, ammonia is most preferred because it can be readily removed from the powder by volatilization. Commercially available aqueous ammonia may be used.

With stirring, an organotrialkoxysilane is dumped into or added dropwise to a water dispersion of silicone elastomer spherical fine particles to which an alkaline substance has been added. The organotrialkoxysilane has the formula: $R^5Si(OR^6)_3$ wherein $R^5$ is a substituted or unsubstituted, monovalent hydrocarbon group of 1 to 20 carbon atoms, and $R^6$ is an unsubstituted monovalent hydrocarbon group of 1 to 6 carbon atoms. Suitable groups of $R^5$ are as exemplified above, and suitable groups of $R^6$ include methyl, ethyl, propyl, butyl, pentyl and hexyl, with methyl being preferred for reactivity. If it is desired to incorporate units $R^5_2SiO_{2/2}$ into the polyorganosilsesquioxane, a silane of the formula: $R^5_2Si(OR^6)_2$ may be added at the same time. The amount of organotrialkoxysilane added is such that in the coated particles, 0.5 to 25 pbw of polyorganosilsesquioxane is present per 100 pbw of silicone elastomer spherical particles.

The dispersion is agitated when the organotrialkoxysilane is added thereto. Vigorous agitation may cause particles to agglomerate together, interfering with coating of discrete particles with polyorganosilsesquioxane. The dispersion may be moderately agitated using propellers or flat paddles although agitation must be at such a strength that the organotrialkoxysilane may be dispersed in the water dispersion of silicone elastomer particles.

When the organotrialkoxysilane is added, the water dispersion of silicone elastomer particles is preferably at a temperature of 0 to 60° C., more preferably 0 to 40° C. Below 0° C., the water dispersion freezes. Above 60° C., particles may agglomerate together, interfering with coating of particles with polyorganosilsesquioxane.

The fine particles comprising silicone elastomer spherical fine particles coated with polyorganosilsesquioxane according to the invention are water repellent. To further enhance water repellency, hydrolytic condensation reaction between a tetraalkoxysilane and at least one silylating agent selected from trimethylalkoxysilane, trimethylsilanol and hexamethyldisilazane is preferably carried out on the surface of a coating of polyorganosilsesquioxane. Hydrolytic condensation reaction of trimethylalkoxysilane, trimethylsilanol and/or hexamethyldisilazane introduces trimethylsilyl groups to the surface of polyorganosilsesquioxane to improve water repellency. To form more trimethylsilyl groups on the surface of polyorganosilsesquioxane, hydrolytic condensation reaction of tetraalkoxysilane is carried out on that surface according to the invention. Specifically, tetraalkoxysilane is subjected to hydrolytic condensation reaction on the surface of polyorganosilsesquioxane to form more silanol and/or alkoxysilyl groups with which trimethylalkoxysilane, trimethylsilanol and/or hexamethyldisilazane are able to react, thereby eventually increasing the number of trimethylsilyl groups introduced.

The tetraalkoxysilane has the formula: $Si(OR^7)_4$ wherein $R^7$ which may be the same or different is alkyl of 1 to 6 carbon atoms, for example, such as methyl, ethyl, propyl, butyl, pentyl or hexyl, with methyl being most preferred. The trimethylalkoxysilane has the formula: $(CH_3)_3SiOR^8$ wherein $R^8$ which may be the same or different is alkyl of 1 to 6 carbon atoms, for example, such as methyl, ethyl, propyl, butyl, pentyl or hexyl, with methyl being most preferred. The trimethylsilanol has the formula: $(CH_3)_3SiOH$, and hexamethyldisilazane has the formula: $[(CH_3)_3Si]_2NH$.

An appropriate amount of trimethylalkoxysilane, trimethylsilanol and/or hexamethyldisilazane added is 0.1 to 10 parts, more preferably 0.5 to 5 parts by weight per 100 parts by weight of silicone elastomer spherical fine particles. Less than 0.1 pbw may fail to achieve the water repellency enhancing effect whereas more than 10 pbw may achieve no further improvement in water repellency.

An appropriate amount of tetraalkoxysilane added is 0.2 to 1 mole, more preferably 0.3 to 0.5 mole per mole of trimethylalkoxysilane or trimethylsilanol or per 0.5 mole of hexamethyldisilazane. On this basis, less than 0.2 mole may fail to achieve the water repellency enhancing effect whereas more than 1 mole may rather result in a loss of water repellency.

In the preferred embodiment which is intended to further enhance the water repellency of the fine particles comprising silicone elastomer spherical fine particles coated with polyorganosilsesquioxane according to the invention, hydrolytic condensation reaction between a tetraalkoxysilane and trimethylalkoxysilane, trimethylsilanol and/or hexamethyldisilazane is carried out on the surface of polyorganosilsesquioxane coating. After an organotrialkoxysilane is added to a water dispersion of silicone elastomer spherical fine particles and subjected to hydrolytic condensation reaction therein, tetraalkoxysilane and trimethylalkoxysilane, trimethylsilanol and/or hexamethyldisilazane are dumped into or added dropwise to the dispersion which is continuously agitated.

At this point, the tetraalkoxysilane and trimethylalkoxysilane, trimethylsilanol and/or hexamethyldisilazane undergo hydrolytic condensation reaction under the catalysis of the alkaline substance which has been added to the dispersion. However, if the liquid is at lower pH, reaction runs short. In such a case, an additional amount of the alkaline substance may be added to the dispersion before or after the tetraalkoxysilane and trimethylalkoxysilane, trimethylsilanol and/or hexamethyldisilazane are added.

The water dispersion of polyorganosilsesquioxane-coated fine particles is agitated when the tetraalkoxysilane and trimethylalkoxysilane, trimethylsilanol and/or hexamethyldisilazane are added thereto. Vigorous agitation may cause particles to agglomerate together, failing to enhance water repellency. The dispersion may be moderately agitated using propellers or flat paddles although agitation must be at such a strength that the reactants may be dispersed in the water dispersion of polyorganosilsesquioxane-coated particles.

When the tetraalkoxysilane and trimethylalkoxysilane, trimethylsilanol and/or hexamethyldisilazane are added to the water dispersion of polyorganosilsesquioxane-coated particles, the dispersion is preferably at a temperature of 0 to 60° C., more preferably 0 to 40° C. Below 0° C., the water dispersion freezes. Above 60° C., particles may agglomerate together, failing to enhance water repellency.

With respect to the order of addition, the tetraalkoxysilane and the trimethylalkoxysilane, trimethylsilanol and/or hexamethyldisilazane may be simultaneously added to the water dispersion of polyorganosilsesquioxane-coated particles, or the tetraalkoxysilane may be first added and the trimethylalkoxysilane, trimethylsilanol and/or hexamethyldisilazane then added. At the end of addition, agitation is preferably continued for some time until the completion of hydrolytic condensation reaction. The dispersion may be heated at 40 to 100° C. for driving hydrolytic condensation reaction to completion. Thereafter, an acidic substance may be added for neutralization, if necessary.

The fine particles comprising silicone elastomer spherical fine particles coated with polyorganosilsesquioxane according to the invention are water repellent so that they are non-dispersible in water and float on water. Differently stated, the fine particles are water repellent as demonstrated by a contact angle with water of at least 90 deg. Preferably the fine particles are non-dispersible in 30% methanol water and float on the methanol water.

The fine particles comprising silicone elastomer spherical fine particles coated with polyorganosilsesquioxane are endowed with water repellency or an inability to disperse in water by removing the surfactant therefrom. The polyorganosilsesquioxane coating and pendant trimethylsilyl groups display water repellency, but lose water repellency if only a trace amount of surfactant is co-present. Thus the surfactant must be removed.

Removal of the surfactant is carried out by washing. Water washing is inefficient because washing must be repeated many times and a large volume of water is necessary. Also it is difficult to remove the surfactant completely by water washing. Thus washing is done with alcohol, or a mixture of alcohol and water. The alcohol used herein is preferably water soluble and also preferably has a low boiling point because it can be readily removed from the powder by volatilization. Suitable alcohols include methanol, ethanol, 1-propanol, 2-propanol, n-butanol, sec-butanol, tert-butanol, 2-methyl-2-butanol, ethylene glycol, and 2,3-butanediol.

The dispersion is washed by adding alcohol or a mixture of alcohol and water, agitating using an agitator such as a propeller or flat paddle, and removing water by filtration, centrifugation, decantation or the like. The washing operation may be repeated if water repellency is still insufficient. It is also possible to carry out centrifugal dehydration while flowing alcohol or a mixture of alcohol and water. When a mixture of alcohol and water is used, the concentration of alcohol is preferably at least 5% by weight, and more preferably at least 10% by weight.

From the product as washed, water and alcohol residues are removed by heating under atmospheric or reduced pressure. Heat may be applied to the product which may be kept static, agitated or fluidized. A flowing heat medium may also be used. Alternatively, the product may be sprayed and dispersed in a hot air stream using a spray dryer.

If the resulting particles are in agglomerated state, such agglomerates must be disintegrated by a grinding machine such as a jet mill, ball mill or hammer mill.

EXAMPLE

Examples of the invention are given below by way of illustration and not by way of limitation. In Examples, the viscosity is measured at 25° C. All percents as used in conjunction with concentration and content are by weight.

Example 1

A 1-L glass beaker was charged with 500 g of methylvinylpolysiloxane of formula (1), shown below, having a viscosity of 580 mm$^2$/s and 19 g (an amount to provide 1.06 hydrosilyl groups per olefinic unsaturated group) of methylhydrogenpolysiloxane of formula (2), shown below, having a viscosity of 30 mm$^2$/s. Using a homo mixer, the contents were agitated at 2000 rpm for dissolution. Then 3 g of polyoxyethylene lauryl ether (moles of ethylene oxide added=9 moles) and 55 g of water were added. The contents were agitated at 6000 rpm using Homo Mixer until an oil-in-water type emulsion with a noticeable viscosity buildup was formed, after which agitation was continued for a further 15 minutes. While agitating at 2000 rpm, 421 g of water was added to the emulsion, which turned into a homogeneous white emulsion. The emulsion was transferred to a 1-L glass flask equipped with an anchor paddle agitator, where it was conditioned at 15-20° C. With agitation, a mixture of 0.8 g of a toluene solution of chloroplatinic acid-olefin complex (Pt content 0.5%) and 1.6 g of polyoxyethylene lauryl ether (moles of ethylene oxide added=9 moles) was added to the emulsion. The emulsion was agitated for 12 hours at the temperature, yielding a water dispersion of silicone elastomer fine particles. The shape of silicone elastomer particles was found spherical as observed under an optical microscope. The particles had a volume mean particle size of 5 μm as measured by an electric resistance particle size distribution analyzer Multisizer™ 3 (Beckman Coulter Inc.).

The water dispersion of silicone elastomer particles, 870 g, was transferred to a 3-L glass flask equipped with an anchor paddle agitator, to which 2013 g of water and 57 g of 28% aqueous ammonia were added. At this point, the liquid was at pH 11.3. The liquid was conditioned at 5-10° C., and 60 g (an amount to provide 6.5 parts by weight of polymethylsilsesquioxane per 100 parts by weight of silicone elastomer spherical particles after hydrolytic condensation reaction) of methyltrimethoxysilane was added dropwise over 20 minutes. Agitation was continued for a further 1 hour while maintaining the liquid temperature at 5-10° C. The liquid temperature was raised to 55-60° C., at which agitation was continued for 1 hour for driving hydrolytic condensation reaction of methyltrimethoxysilane to completion.

The resulting liquid in which hydrolytic condensation reaction of methyltrimethoxysilane had run in the water dispersion of silicone elastomer particles was dehydrated to a water content of about 30% by a pressure filter. The wet cake was transferred to a 5-L glass flask equipped with an anchor paddle agitator, to which 3000 g of 50% methanol water was added. The liquid was agitated for 30 minutes and dehydrated by a pressure filter. The wet cake was transferred to a 5-L glass flask equipped with an anchor paddle agitator, to which 3000 g of water was added. The liquid was agitated for 30 minutes and dehydrated by a pressure filter. The wet cake was dried in a hot air circulating dryer at 105° C. The dry product was disintegrated by a jet mill, yielding free-flowing fine particles. The fine particles were observed under an electron microscope, finding spherical particles surface covered with grains having a size of about 100 nm. That is, the fine particles were confirmed to be silicone elastomer spherical particles coated with polymethylsilsesquioxane. For particle size measurement, fine particles were dispersed in water with the aid of a surfactant and analyzed by the particle size distribution analyzer Multisizer™ 3 (Beckman Coulter Inc.), finding a volume mean particle size of 5 μm.

Separately, methylvinylpolysiloxane of formula (1), shown below, having a viscosity of 580 mm$^2$/s, methylhydrogenpolysiloxane of formula (2), shown below, having a viscosity of 30 mm$^2$/s, and a toluene solution of chloroplatinic acid-olefin complex (Pt content 0.5%) were mixed in the same proportion as above. The mixture was cast into an aluminum dish to a thickness of 10 mm, allowed to stand at 25° C. for 24 hours, and heated in a thermostat tank at 50° C. for one hour, obtaining a tack-free silicone elastomer. The silicone elastomer had a hardness of 29 as measured by a Durometer A hardness meter.

In a 100-mL beaker containing 50 g of water, a 1-g sample of the fine particles in the form of silicone elastomer particles coated with polymethylsilsesquioxane was admitted. This was agitated with a glass rod for one minute, whereupon the fine particles were not dispersed in water. All the particles remained afloat on water.

In a 100-mL beaker containing 50 g of 30% methanol water, a 1-g sample of the fine particles in the form of silicone elastomer particles coated with polymethylsilsesquioxane was admitted. This was agitated with a glass rod for one minute, whereupon about half fine particles were dispersed in water and about half fine particles remained afloat on water.

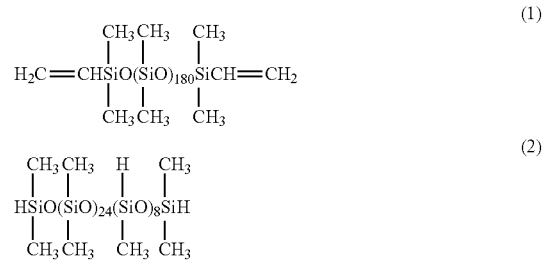

Example 2

A water dispersion of silicone elastomer spherical fine particles was prepared as in Example 1.

The water dispersion of silicone elastomer particles, 870 g, was transferred to a 3-L glass flask equipped with an anchor paddle agitator, to which 2013 g of water and 57 g of 28% aqueous ammonia were added. At this point, the liquid was at pH 11.3. The liquid was conditioned at 5-10° C., and 46.8 g (an amount to provide 5.1 parts by weight of polymethylsilsesquioxane per 100 parts by weight of silicone elastomer particles after hydrolytic condensation reaction) of methyltrimethoxysilane was added dropwise over 20 minutes. Next, a mixture of 8.4 g (corresponding to 1.9 parts by weight relative to 100 parts by weight of silicone elastomer particles) of trimethylsilanol and 4.8 g (corresponding to 0.34 mole per mole of trimethylsilanol) of tetramethoxysilane was added dropwise over 5 minutes. Agitation was continued for a further 1 hour while maintaining the liquid temperature at 5-10° C. The liquid temperature was raised to 55-60° C., at which agitation was continued for 1 hour for driving hydrolytic condensation reaction of methyltrimethoxysilane, tetramethoxysilane and trimethylsilanol to completion.

The resulting liquid in which hydrolytic condensation reaction of methyltrimethoxysilane, tetramethoxysilane and trimethylsilanol had run in the water dispersion of silicone elastomer particles was dehydrated to a water content of about 30% by a pressure filter. The wet cake was transferred to a 5-L glass flask equipped with an anchor paddle agitator, to which 3000 g of 50% methanol water was added. The liquid was agitated for 30 minutes and dehydrated by a pressure filter. The wet cake was transferred to a 5-L glass flask equipped with an anchor paddle agitator, to which 3000 g of water was added. The liquid was agitated for 30 minutes and dehydrated by a pressure filter. The wet cake was dried in a hot air circulating dryer at 105° C. The dry product was disintegrated by a jet mill, yielding free-flowing fine particles. The fine particles were observed under an electron microscope, finding spherical particles surface covered with grains having a size of about 100 nm. That is, the fine particles were confirmed to be silicone elastomer spherical particles coated with polymethylsilsesquioxane. For particle size measurement, fine particles were dispersed in water with the aid of a surfactant and analyzed by the particle size distribution analyzer Multisizer™ 3 (Beckman Coulter Inc.), finding a volume mean particle size of 5 μm.

In a 100-mL beaker containing 50 g of water, a 1-g sample of the fine particles in the form of silicone elastomer particles coated with polymethylsilsesquioxane was admitted. This was agitated with a glass rod for one minute, whereupon the fine particles were not dispersed in water. All the particles remained afloat on water.

In a 100-mL beaker containing 50 g of 30% methanol water, a 1-g sample of the fine particles in the form of silicone elastomer particles coated with polymethylsilsesquioxane was admitted. This was agitated with a glass rod for one minute, whereupon the fine particles were not dispersed in water. All the particles remained afloat on water.

Example 3

A water dispersion of silicone elastomer spherical fine particles was prepared as in Example 1.

The water dispersion of silicone elastomer particles, 870 g, was transferred to a 3-L glass flask equipped with an anchor paddle agitator, to which 2012 g of water and 57 g of 28% aqueous ammonia were added. At this point, the liquid was at pH 11.3. The liquid was conditioned at 5-10° C., and 46.8 g (an amount to provide 5.1 parts by weight of polymethylsilsesquioxane per 100 parts by weight of silicone elastomer particles after hydrolytic condensation reaction) of methyltrimethoxysilane was added dropwise over 20 minutes. Next, a mixture of 9.9 g (corresponding to 2.2 parts by weight relative to 100 parts by weight of silicone elastomer particles) of trimethylmethoxysilane and 4.8 g (corresponding to 0.33 mole per mole of trimethylmethoxysilane) of tetramethoxysilane was added dropwise over 5 minutes. Agitation was continued for a further 1 hour while maintaining the liquid temperature at 5-10° C. The liquid temperature was raised to 55-60° C., at which agitation was continued for 1 hour for driving hydrolytic condensation reaction of methyltrimethoxysilane, tetramethoxysilane and trimethylmethoxysilane to completion.

The resulting liquid in which hydrolytic condensation reaction of methyltrimethoxysilane, tetramethoxysilane and trimethylmethoxysilane had run in the water dispersion of silicone elastomer particles was dehydrated to a water content of about 30% by a pressure filter. The wet cake was transferred to a 5-L glass flask equipped with an anchor paddle agitator, to which 3000 g of 50% methanol water was added. The liquid was agitated for 30 minutes and dehydrated by a pressure filter. The wet cake was transferred to a 5-L glass flask equipped with an anchor paddle agitator, to which 3000 g of water was added. The liquid was agitated for 30 minutes and dehydrated by a pressure filter. The wet cake was dried in a hot air circulating dryer at 105° C. The dry product was disintegrated by a jet mill, yielding free-flowing fine particles. The fine particles were observed under an electron microscope, finding spherical particles surface covered with grains having a size of about 100 nm. That is, the fine particles were confirmed to be silicone elastomer spherical particles coated with polymethylsilsesquioxane. For particle size measurement, fine particles were dispersed in water with the aid of a surfactant and analyzed by the particle size distribution analyzer Multisizer™ 3 (Beckman Coulter Inc.), finding a volume mean particle size of 5 μm.

In a 100-mL beaker containing 50 g of water, a 1-g sample of the fine particles in the form of silicone elastomer particles coated with polymethylsilsesquioxane was admitted. This was agitated with a glass rod for one minute, whereupon the fine particles were not dispersed in water. All the particles remained afloat on water.

In a 100-mL beaker containing 50 g of 30% methanol water, a 1-g sample of the fine particles in the form of silicone elastomer particles coated with polymethylsilsesquioxane was admitted. This was agitated with a glass rod for one minute, whereupon the fine particles were not dispersed in water. All the particles remained afloat on water.

Example 4

A water dispersion of silicone elastomer spherical fine particles was prepared as in Example 1.

The water dispersion of silicone elastomer particles, 870 g, was transferred to a 3-L glass flask equipped with an anchor paddle agitator, to which 2014 g of water and 57 g of 28% aqueous ammonia were added. At this point, the liquid was at pH 11.3. The liquid was conditioned at 5-10° C., and 46.8 g (an amount to provide 5.1 parts by weight of polymethylsilsesquioxane per 100 parts by weight of silicone elastomer particles after hydrolytic condensation reaction) of methyltrimethoxysilane was added dropwise over 20 minutes. Next, a mixture of 7.6 g (corresponding to 1.7 parts by weight relative to 100 parts by weight of silicone elastomer particles) of hexamethyldisilazane and 4.8 g (corresponding to 0.33 mole per mole of hexamethyldisilazane) of tetramethoxysilane was added dropwise over 5 minutes. Agitation was continued for a further 1 hour while maintaining the liquid temperature at 5-10° C. The liquid temperature was raised to 55-60° C., at which agitation was continued for 1 hour for driving hydrolytic condensation reaction of methyltrimethoxysilane, tetramethoxysilane and hexamethyldisilazane to completion.

The resulting liquid in which hydrolytic condensation reaction of methyltrimethoxysilane, tetramethoxysilane and hexamethyldisilazane had run in the water dispersion of silicone elastomer particles was dehydrated to a water content of about 30% by a pressure filter. The wet cake was transferred to a 5-L glass flask equipped with an anchor paddle agitator, to which 3000 g of 50% methanol water was added. The liquid was agitated for 30 minutes and dehydrated by a pressure filter. The wet cake was transferred to a 5-L glass flask equipped with an anchor paddle agitator, to which 3000 g of water was added. The liquid was agitated for 30 minutes and dehydrated by a pressure filter. The wet cake was dried in a hot air circulating dryer at 105° C. The dry product was disintegrated by a jet mill, yielding free-flowing fine particles. The fine particles were observed under an electron microscope, finding spherical particles surface covered with grains having a size of about 100 nm. That is, the fine particles were confirmed to be silicone elastomer spherical particles coated with polymethylsilsesquioxane. For particle size measurement, fine particles were dispersed in water with the aid of a surfactant and analyzed by the particle size distribution analyzer Multisizer™ 3 (Beckman Coulter Inc.), finding a volume mean particle size of 5 µm.

In a 100-mL beaker containing 50 g of water, a 1-g sample of the fine particles in the form of silicone elastomer particles coated with polymethylsilsesquioxane was admitted. This was agitated with a glass rod for one minute, whereupon the fine particles were not dispersed in water. All the particles remained afloat on water.

In a 100-mL beaker containing 50 g of 30% methanol water, a 1-g sample of the fine particles in the form of silicone elastomer particles coated with polymethylsilsesquioxane was admitted. This was agitated with a glass rod for one minute, whereupon the fine particles were not dispersed in water. All the particles remained afloat on water.

Comparative Example 1

The liquid in which hydrolytic condensation reaction of methyltrimethoxysilane had run in the water dispersion of silicone elastomer particles in Example 1 was dehydrated to a water content of about 30% by a pressure filter. The wet cake was transferred to a 5-L glass flask equipped with an anchor paddle agitator, to which 3000 g of water was added. The liquid was agitated for 30 minutes and dehydrated by a pressure filter. The wet cake was transferred to a 5-L glass flask equipped with an anchor paddle agitator, to which 3000 g of water was added. The liquid was agitated for 30 minutes and dehydrated by a pressure filter. The wet cake was dried in a hot air circulating dryer at 105° C. The dry product was disintegrated by a jet mill, yielding free-flowing fine particles. The fine particles were observed under an electron microscope, finding spherical particles surface covered with grains having a size of about 100 nm. That is, the fine particles were confirmed to be silicone elastomer spherical particles coated with polymethylsilsesquioxane. For particle size measurement, fine particles were dispersed in water with the aid of a surfactant and analyzed by the particle size distribution analyzer Multisizer™ 3 (Beckman Coulter Inc.), finding a volume mean particle size of 5 µm.

In a 100-mL beaker containing 50 g of water, a 1-g sample of the fine particles in the form of silicone elastomer particles coated with polymethylsilsesquioxane was admitted. This was agitated with a glass rod for one minute, whereupon all the fine particles were dispersed in water.

Comparative Example 2

The liquid in which hydrolytic condensation reaction of methyltrimethoxysilane, tetramethoxysilane and trimethylsilanol had run in the water dispersion of silicone elastomer particles in Example 2 was dehydrated to a water content of about 30% by a pressure filter. The wet cake was transferred to a 5-L glass flask equipped with an anchor paddle agitator, to which 3000 g of water was added. The liquid was agitated for 30 minutes and dehydrated by a pressure filter. The wet cake was transferred to a 5-L glass flask equipped with an anchor paddle agitator, to which 3000 g of water was added. The liquid was agitated for 30 minutes and dehydrated by a pressure filter. The wet cake was dried in a hot air circulating dryer at 105° C. The dry product was disintegrated by a jet mill, yielding free-flowing fine particles. The fine particles were observed under an electron microscope, finding spherical particles surface covered with grains having a size of about 100 nm. That is, the fine particles were confirmed to be silicone elastomer spherical particles coated with polymethylsilsesquioxane. For particle size measurement, fine particles were dispersed in water with the aid of a surfactant and analyzed by the particle size distribution analyzer Multisizer™ 3 (Beckman Coulter Inc.), finding a volume mean particle size of 5 µm.

In a 100-mL beaker containing 50 g of water, a 1-g sample of the fine particles in the form of silicone elastomer particles coated with polymethylsilsesquioxane was admitted. This was agitated with a glass rod for one minute, whereupon all the fine particles were dispersed in water.

The fine particles in the form of silicone elastomer particles coated with polymethylsilsesquioxane from which the surfactant was removed by washing with methanol/water in Example 1 were water repellent. The fine particles obtained by effecting hydrolytic condensation reaction of tetraalkoxysilane with trimethylalkoxysilane, trimethylsilanol or hexamethyldisilazane on the surface of polymethylsilsesquioxane coating and washing with methanol/water in Examples 2 to 4 were more water repellent. These fine particles are expected to prevent a makeup smearing phenomenon when formulated in cosmetics. By contrast, the fine particles obtained only by water washing in Comparative Examples 1 and 2 are not water repellent on account of the residual surfactant, and the desired effect is not expectable.

Although some preferred embodiments have been described, many modifications and variations may be made thereto in light of the above teachings. It is therefore to be understood that the invention may be practiced otherwise than as specifically described without departing from the scope of the appended claims.

What is claimed is:
1. A method for preparing water repellent fine particles comprising the steps of
   providing a dispersion of silicone elastomer spherical particles having a volume mean particle size of 0.1 to 100 µ in water using a surfactant,
   adding an organotrialkoxysilane to the dispersion and effecting hydrolytic condensation reaction thereof in the dispersion in the presence of an alkaline substance for coating the silicone elastomer particles with polyorganosilsesquioxane,
   adding a tetraalkoxysilane and at least one silylating agent selected from trimethylalkoxysilane, trimethylsilanol and hexamethyldisilazane to the dispersion and effecting hydrolytic condensation reaction thereof in the dispersion, and
   washing the coated particles with alcohol or a mixture of alcohol and water to remove the surfactant,
   thereby obtaining the water repellent fine particles being non-dispersible in water and floatable on water.

2. The method of claim 1, wherein the alkaline substance is previously added to the dispersion in such amounts that the pH of the resulting dispersion is in a range of 10.0 to 13.0.

3. The method of claim 1, wherein the alkaline substance is ammonia.

4. The method of claim 1, wherein the amount of organotrialkoxysilane added is such that in the coated particles, 0.5 to 25 parts by weight of polyorganosilsesquioxane is present per 100 parts by weight of silicone elastomer spherical particles.

5. The method of claim 1, wherein when the organotrialkoxysilane is added to the dispersion of silicone elastomer spherical particles in water, the dispersion is at a temperature of 0 to 60° C.

6. The method of claim 1, wherein the amount of trimethylalkoxysilane, trimethylsilanol and/or hexamethyldisilazane added is 0.1 to 10 parts by weight per 100 parts by weight of silicone elastomer spherical fine particles.

7. The method of claim 1, wherein the amount of tetraalkoxysilane added is 0.2 to 1 mole per mole of trimethylalkoxysilane or trimethylsilanol or per 0.5 mole of hexamethyldisilazane.

8. The method of claim 1, wherein when the tetraalkoxysilane and trimethylalkoxysilane, trimethylsilanol and/or hexamethyldisilazane are added to the water dispersion of polyorganosilsesquioxane-coated particles, the dispersion is at a temperature of 0 to 60° C.

9. The method of claim 1, wherein the silicone elastomer has rubber elasticity and is a tack-free cured form of silicone compound comprising linear organosiloxane blocks of the formula

wherein $R^1$ is an optionally substituted monovalent hydrocarbon group of 1 to 30 carbon atoms and n is a positive number of 5 to 5000.

10. The method of claim 9, wherein the silicone elastomer has a rubber hardness of 5 to 90 as measured by type A Durometer according to JIS K-6253.

11. The method of claim 1, wherein the surfactant is a polyoxyethylene alkyl ether.

12. The method of claim 1, wherein the silicone elastomer spherical particles have a volume mean particle size of 1 to 40 μm.

13. The method of claim 1, wherein the organotrialkoxysilane has the formula

wherein $R^5$ is an optionally substituted monovalent hydrocarbon group of 1 to 20 carbon atoms and $R^6$ is an unsubstituted monovalent hydrocarbon group of 1 to 6 carbon atoms.

14. The method of claim 1, wherein the tetraalkoxysilane has the formula

wherein the $R^7$ moieties, which may be the same or different, are alkyl of 1 to 6 carbon atoms.

15. The method of claim 1, wherein the coated particles are washed with the mixture of alcohol and water and the concentration of alcohol in said mixture is 5 to 50% by weight.

16. The method of claim 15, wherein the alcohol is methanol.

17. A method for preparing water repellent fine particles comprising the steps of mixing an organopolysiloxane containing at least two monovalent olefinic unsaturated groups in a molecule and an organohydrogenpolysiloxane containing at least three silicon-bonded hydrogen atoms in a molecule, or an organopolysiloxane containing at least three monovalent olefinic unsaturated groups in a molecule and an organohydrogenpolysiloxane containing at least two silicon-bonded hydrogen atoms in a molecule, adding water and a surfactant to the mixture to form an emulsion of the polysiloxanes, effecting addition polymerization of the polysiloxanes in the presence of a platinum catalyst, thereby obtaining a dispersion of silicone elastomer spherical particles having a volume mean particle size of 0.1 to 100 μm in water with the surfactant, adding an organotrialkoxysilane to the dispersion and effecting hydrolytic condensation reaction thereof in the dispersion in the presence of an alkaline substance for coating the silicone elastomer particles with polyorganosilsesquioxane, adding a tetraalkoxysilane and at least one silylating agent selected from trimethylalkoxysilane, trimethylsilanol, and hexamethyldisilazane to the dispersion and effecting hydrolytic condensation reaction thereof in the dispersion, and washing the coated particles with alcohol or a mixture of alcohol and water to remove the surfactant, thereby obtaining the water repellent fine particles being non-dispersible in water and floatable on water.

18. The method of claim 17, wherein the amount of trimethylalkoxysilane, trimethylsilanol, and/or hexamethyldisilazane added is 0.1 to 10 parts by weight per 100 parts by weight of silicone elastomer spherical fine particles.

19. The method of claim 17, wherein the amount of tetraalkoxysilane added is 0.2 to 1 mole per mole of trimethylalkoxysilane or trimethylsilanol or per 0.5 mole of hexamethyldisilazane.

20. The method of claim 17, wherein when the tetraalkoxysilane and trimethylalkoxysilane, trimethylsilanol, and/or hexamethyldisilazane are added to the water dispersion of polyorganosilsesquioxane-coated particles, the dispersion is at a temperature of 0 to 60° C.

21. The method of claim 17, wherein the coated particles are washed with the mixture of alcohol and water and the concentration of alcohol in said mixture is 5 to 50% by weight.

* * * * *